(12) United States Patent
Binder

(10) Patent No.: US 9,096,911 B2
(45) Date of Patent: Aug. 4, 2015

(54) GRAIN MILLING PROCESS

(75) Inventor: Thomas P. Binder, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 448 days.

(21) Appl. No.: 13/521,365

(22) PCT Filed: Jan. 19, 2011

(86) PCT No.: PCT/US2011/021601
§ 371 (c)(1),
(2), (4) Date: Jul. 10, 2012

(87) PCT Pub. No.: WO2011/097070
PCT Pub. Date: Aug. 11, 2011

(65) Prior Publication Data
US 2013/0102045 A1  Apr. 25, 2013

Related U.S. Application Data

(60) Provisional application No. 61/300,856, filed on Feb. 3, 2010.

(51) Int. Cl.
| | |
|---|---|
| *C13K 13/00* | (2006.01) |
| *C13B 10/00* | (2011.01) |
| *C08B 30/12* | (2006.01) |
| *C08L 1/02* | (2006.01) |
| *C08L 97/00* | (2006.01) |
| *C12P 7/10* | (2006.01) |

(52) U.S. Cl.
CPC ............. *C13K 13/00* (2013.01); *C08B 30/12* (2013.01); *C08L 1/02* (2013.01); *C08L 97/00* (2013.01); *C13B 10/003* (2013.01); *A23V 2002/00* (2013.01); *C12P 7/10* (2013.01); *C12P 2203/00* (2013.01); *Y02E 50/16* (2013.01)

(58) Field of Classification Search
None
See application file for complete search history.

(56) References Cited

U.S. PATENT DOCUMENTS 7,452,425 B1 * 11/2008 Langhauser .................... 127/40

* cited by examiner

*Primary Examiner* — Anand Desai
(74) *Attorney, Agent, or Firm* — William B. Miller

(57) ABSTRACT

A modification is described of a dry grind process for producing ethanol and other co-products from whole grain, whereby the mash is thermochemically treated by cooking the mash in the presence of an organic acid. The organic acid effectively hydrolyzes both the starch and hemicellulosic components in the milled corn to provide fermentable sugars from both the endosperm and other parts of the kernel, without, however, also producing fermentation-inhibiting levels of other known products of the acid hydrolysis of hemicellulosic materials, such as hydroxymethylfurfural (HMF) and furfural. Further, the organic acid is able to solubilize both the starch and the more recalcitrant hemicelluloses while only partially hydrolyzing the same, so that most of the starch and hemicelluloses are hydrolyzed to oligomers and the amount of chemically labile and reducing sugars is kept sufficiently low as to also not appreciably interfere with the fermentation to ethanol.

6 Claims, 1 Drawing Sheet

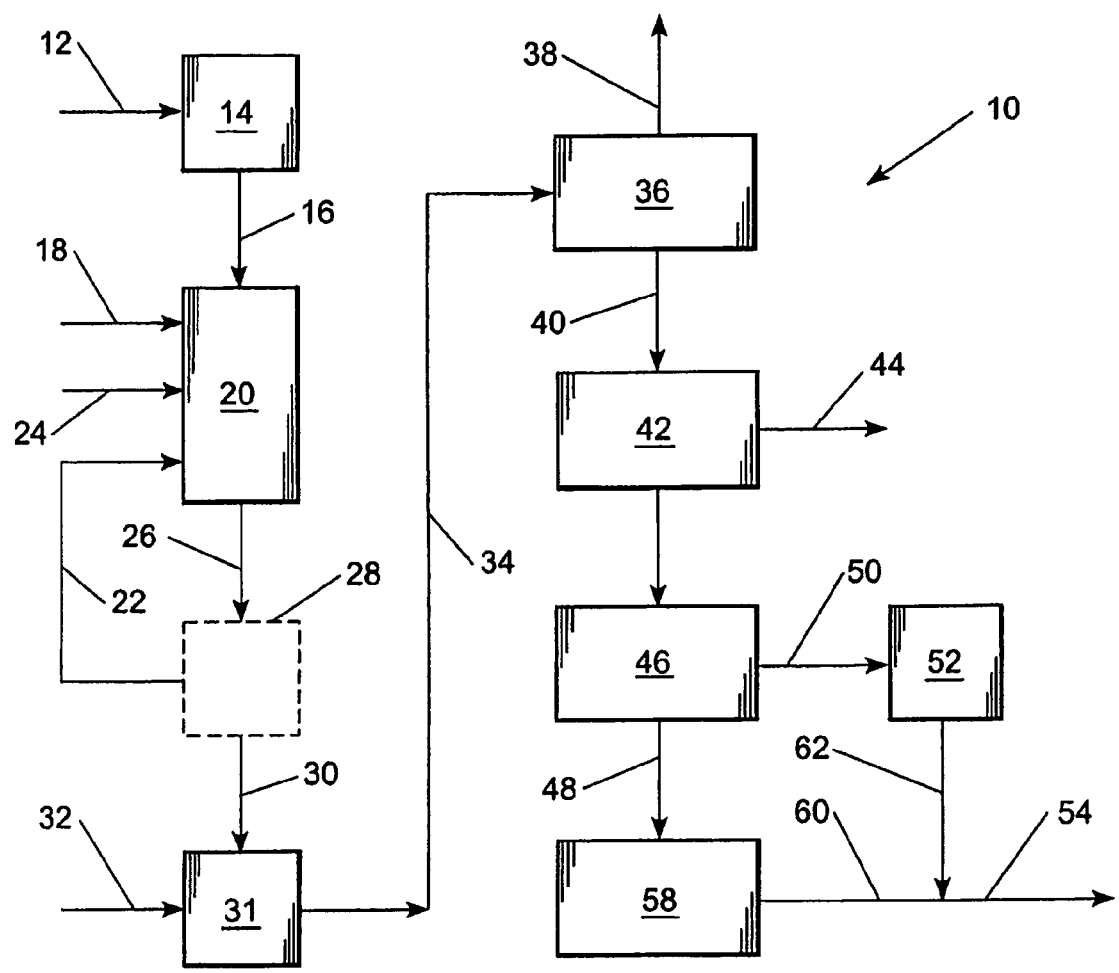

GRAIN MILLING PROCESS

This invention concerns an improved grain milling process, and especially an improved process for the milling of grain, and especially for the milling of corn, for producing ethanol and other value-added products.

Increased demand for ethanol as a fuel additive has in recent years led to a dramatic growth in ethanol production. Currently ethanol is produced mainly from corn by either wet milling or dry grind processing. Wet milling plants are capital intensive and use large amounts of process water, but through fractionation of the corn into its germ, fiber, protein and starch components are able to produce a number of value-added coproducts with ethanol, including high fructose corn syrup, corn gluten meal, corn gluten feed, germ meal and corn oil but also including modified starches, maltodextrins and other materials.

Wet milling ethanol methods conventionally involve five basic processing steps: steeping, germ recovery, fiber recovery, protein recovery and starch washing with subsequent fermentation. In the first step, corn is steeped in a solution of weak sulfurous acid to hydrate and soften the kernel for subsequent separation/fractionation and to leach solubles (water-soluble amino acids and proteins) from the germ. After steeping, germ and fiber fractions are removed by differences in density and particle size. Germ, having a lower density than the remaining solid components of the kernel following the steeping step, is removed by a system of hydroclones, then pressed and dried. Where desired, corn oil can be pressed and/or solvent-extracted from the germ and then refined as a further coproduct. The fiber fraction, containing the pericarp of the kernel, is removed by screening, then contacted with the evaporation-concentrated steepwater from the steeping step. This mixture is then dried to yield a corn gluten feed coproduct.

The remaining solids are then separated into a starch fraction and a protein fraction, through a system of centrifuges and hydroclones. The gluten protein fraction is concentrated using a gluten thickener centrifuge and further dewatered by vacuum belt filtration and drying with rotary steam tube or flash dryers. The final dried product, corn gluten meal, has a high protein and low fiber content, and is used primarily in nonruminant and companion animal diets. The starch recovered by the hydroclone is cooked, liquefied and saccharified to yield glucose, which then undergoes fermentation to the desired primary ethanol product. The ethanol is distilled away from the water and residual water-soluble solids. The recovered residual solids can be added to the corn gluten feed, while carbon dioxide produced in the fermentation can be marketed to the beverage industry.

By contrast, dry grind processing methods are much less capital intensive than are wet milling ethanol methods, in that the corn kernel is not fractionated into its primary parts but is handled whole, and do not require large amounts of process water.

Dry grind ethanol methods also have certain disadvantages, however, as compared to wet milling ethanol methods. Processing the entire kernel, including the non-starch portions of the kernel, is less efficient for producing ethanol. As well, dry grind ethanol processes primarily provide one marketable but relatively lower value coproduct, in the form of distillers' dried grains with solubles (DDGS). The non-fermentable portions in a dry grind ethanol process do contain a fairly high oil content, but recovery is difficult.

Briefly, in a typical dry grind ethanol process, whole corn is ground, slurried with water and cooked with the addition of enzymes to yield a liquefied "mash". Yeast and enzymes are added to the mash, and the mash undergoes concurrent saccharification and fermentation to yield the desired primary ethanol product in a liquid portion, while the unfermented solids left over are recovered with the yeast as distillers' dried grains. Carbon dioxide from the fermentation is released from the broth in a vapor liquid separator, and the ethanol is recovered from the liquid portion for use as a fuel additive.

A variation of the typical process first treats the corn with cold water, hot water and/or steam for a time, increasing the moisture content of the corn from 15% to 22%, in order to soften the bran/pericarp and germ and allow their separation from the starchy endosperm tissue of the kernel. The corn is sent through an abrasion/degermination step to break the kernels into pericarp, germ and endosperm fractions. After drying, an aspiration step separates the pericarp from the endosperm, while a gravity table is used to separate the germ fraction from the endosperm. The endosperm is then ground and processed in the same way as in a typical dry grind process. While the soaking, degermination, aspiration and density separation steps and equipment require additional capital, this variation of a dry grind process is considered advantaged as compared to the typical process described above, in that additional coproduct value can be obtained in the form of corn oil (from the germ) and animal feed value from the pericarp and oil cake.

In sum, then, wet milling ethanol methods offer additional coproduct opportunities as compared to the above-described dry grind methods, but require significant investments of capital and process water resources and involve much greater complexity in operation. Additionally, one of the principal coproducts of wet milling—high fructose corn syrup—has been argued by some to be a significant contributor to obesity. Dry grind methods are simpler and require less capital and water, but produce less value in the way of coproducts and are less efficient generally in terms of extracting full value from the various component parts of the corn kernel.

An improved milling process for producing fuel additive quality ethanol from a grain such as corn, for example, would possess the desirable attributes in both wet milling and dry grind methods, namely, the ability to fractionate and derive value from all parts of the corn kernel that characterizes wet milling, while retaining the simplicity and lower capital and water resource demands of dry grind processing.

Generally, the present invention provides improved methods for the processing of grain and grain products to obtain greater value therefrom in a dry grind ethanol process. Thus, while the description hereafter will describe such improved methods in the context of preferred embodiments, in processing corn particularly, those skilled in the art will recognize that the methods can be beneficially applied to other grains such as wheat, millet, barley, sorghum, triticale, rice, amaranth, buckwheat, rye, oats and quinoa.

The present invention provides needed improvements through a simple modification of a typical dry grind process whereby the mash is thermochemically treated, by cooking the mash in the presence of an organic acid. The organic acid effectively hydrolyzes both the starch and hemicellulosic components in the milled corn to provide fermentable sugars from both the endosperm and other parts of the kernel, without, however, also producing fermentation-inhibiting levels of other known products of the acid hydrolysis of hemicellulosic materials, such as hydroxymethylfurfural (HMF) and furfural. Further, the organic acid (and "organic acid" will be understood as encompassing both individual acids as well as mixtures of organic acids) is able to solubilize both the starch and the more recalcitrant hemicelluloses while only partially hydrolyzing the same, so that most of the starch and hemicelluloses are hydrolyzed to oligomers and the amount of chemically labile and reducing sugars is kept sufficiently low as to also not appreciably interfere with the fermentation to ethanol.

FIG. 1 depicts an improved grain milling process of the present invention, in one illustrative embodiment.

In preferred embodiments of the invention, a typical dry grind process, wherein whole corn is ground, slurried with water, treated with enzymes and cooked to form a liquefied mash, then is treated with additional enzymes, fermented and further processed to yield fuel grade-additive quality ethanol and other products, is modified to incorporate an organic acid such as acetic acid or formic acid (or a combination of these) into the "mashing" step. An acid recovery step is optionally but preferably interposed as a further, limited modification, to recover organic acid from the mash prior to the addition of yeast and additional enzymes for carrying out the fermentation of the mash.

By introducing an organic acid preferably with the water in the form of an aqueous organic acid solution, starch and hemicellulosic components of the corn are solubilized and partially hydrolyzed as summarized above. By forming fermentable $C_5$ sugars from the hemicelluloses present in the kernel (especially in the pericarp), the overall ethanol yield from the kernel can be improved.

Further, because the organic acids are not strong acids, HMF (hydroxymethylfurfural) and furfural—both known byproducts of acid hydrolyzing hemicellulosic materials but also both being known inhibitors of enzymatic activity in bioethanol production by fermentation—can be avoided at levels that would tend to undesirably interfere with or inhibit the subsequent fermentation of the $C_5$ and $C_6$ sugars to ethanol. As well, the amount of chemically labile free sugars or reducing sugars can be kept low, to avoid chemical inhibitors to yeast and sugar loss.

The organic acids preferably provide additional opportunities to gain value from the proteins and oil present in the corn kernel, too. In regards to the recovery of oil from the corn, extracting oil from whole corn has to date been an expensive and inefficient proposition because the oil is mainly present in the germ and as a result is present in a low concentration in ground corn as a whole.

BRIEF DESCRIPTION OF THE DRAWING

The use of a moderate concentration aqueous organic acid solution, for example, 50% formic acid in water, to cook (at 90 degrees Celsius and ambient pressure) a 30 to 40% total solids corn slurry to which amylase enzymes have been added, has been demonstrated below to solubilize 85% of the corn solids into an aqueous phase which is easily separated from the residual solids by centrifugation or filtration. These residual solids have a high enough oil concentration to make recovery of the corn oil from whole kernel processing now economical. Further, after the oil is conventionally recovered by pressing or extraction, the residual solids are found to have a high protein content as the corn proteins are not solubilized by the organic acids of our invention. Such high protein solids are desirable for use in animal feeds, but in contrast to the distillers' dried grains which are well-suited only for ruminants, the residual solids provided by our process will in preferred embodiments be suited for use in feeds for non-ruminants such as poultry and hogs.

The present invention is illustrated and understood more fully by reference to FIG. 1, in which a modified dry grind ethanol process 10 is shown in a preferred embodiment. The embodiment 10 is intended to be illustrative only, and those skilled in the art will readily appreciate that numerous modifications and variations to the embodiment 10 may be made as well as that the present invention may be adapted for use with a variety of existing or known dry grind methods, without departing from the proper scope of the invention as defined more particularly by the claims following hereafter.

Returning now to FIG. 1, as shown, whole corn 12 is milled or ground in a milling step 14. Milling may be done by any known method, for example by use of a Fitz mill, Beall degerminator or Satake degerminator. Milling step 14 produces a ground corn stream 16, which is a heterogeneous mixture including germ, endosperm, pericarp and fines. The fines are primarily starch, and the pericarp is primarily fibrous material.

Ground corn stream 16 is slurried with water 18, and is cooked into a mash in mashing step 20 in the presence of an organic acid 22 (whether supplied anew or generated largely from optional acid recovery step 28 with makeup acid being supplied anew as needed) and with addition of an enzyme 24 to aid in the liquefaction of fermentable components of the corn. Typically the ground corn stream 16 is combined with a volume of water 18 having a weight of two to three times the weight of the corn to be mashed, the water 18 usually being supplied in a typical dry grind process in the form of fermentation backset, condensed evaporator water or corn steep liquor. The organic acid 22 is preferably acetic acid or formic acid, preferably being supplied with some of the water 18 as a moderate concentration to more highly concentrated aqueous acid solution. A preferred concentration, range is from 50 percent by weight to 70 percent by weight, while more preferably the acid solution will be closer to 50 percent acid.

The corn, water and acid mixture is preferably maintained at a temperature between 70 degrees and 90 degrees Celsius (and more preferably at a temperature of from 88 to 90 degrees Celsius) for approximately 30 minutes, after which α-amylase enzyme is added (indicated by stream 24) and the temperature raised to from 105 to 110 degrees Celsius for from 5 to 15 minutes, to aid in the liquefaction of starch and hemicellulose materials from primarily the endosperm and pericarp. The addition of the enzyme combined with heating causes breakdown of the starch to maltooligosaccharides, as in typical dry grind methods. The organic acid, however, additionally hydrolyzes (thermochemically treats) the hemicelluloses in the pericarp, previously consigned only to the lower value distillers dried grains coproduct, and provides $C_5$ sugars which add to the fermentable content of the mash stream 26 proceeding from the mashing step 20.

The mash 26 then proceeds to an optional acid recovery step 28, wherein the organic acid may be recovered if desired and preferably recycled to provide at least a portion of the acid stream 22. The acid recovery step 28 may take various forms, depending, for example, on the organic acid used and on its concentration in the mash stream 26. In this regard, formic acid is known to form an azeotrope with water at concentrations on the order of 50 percent by weight, whereas acetic acid does not, so that either of azeotropic distillation or conventional distillation may be desirably employed dependent on the circumstances of use. In any case, those skilled in the art should be wellable to select an economical acid recovery technique for step 28, if acid recovery is considered important.

The temperature of the mash 30 following the acid recovery step 28 is reduced to between 60 and 75 degrees, and glucoamylase enzyme (shown as stream 32) is added in step 31 to further produce glucose from the starchy endosperm of the corn kernel, while maintaining a temperature of between 60 and 75 degrees over a period of from 1 to 48 hours.

The resultant fermentation medium 34 then is fermented in fermentation step 36 with addition of glucoamylase enzyme and of a fermentative microorganism, which microorganism can be, for example, a yeast (e.g., *saccharomyces cerevisiae*), bacteria or fungus, such fermentation typically occurring at a temperature of from 30 to 40 degrees Celsius. Typical manufacturer-recommended glucoamylase addition levels may be used, for example, on the order of 0.22 units per gram of starch. Other enzymes may also be added including hemicellulases, proteases, cellulases, and feruloyl esterases.

The fermentation results in the production of a carbon dioxide product stream 38, ethanol and various non-fermentable solids and residues, including yeast, gluten proteins, germ and fiber. After allowing the carbon dioxide to release from the fermentation broth as stream 38, the ethanol and remaining solids are passed (reference number 40) to a distillation step 42, whereby the crude ethanol stream 44 from the fermentation is recovered for further clean-up and purification (not shown) prior to use as a fuel additive.

The remaining water and solids from the fermentation step 36 undergo a liquids/solids separation as, for example, in a centrifugation step 46, resulting in a solids portion 48 containing the oil-bearing germ and other solids and a thin stillage portion 50 which is preferably concentrated by evaporation in step 52 for being incorporated in a high protein feed product 54. The considerable oil content in solids portion 48 is extracted as a crude corn oil coproduct stream 56 for further refining not shown), by means of oil recovery step 58.

Oil recovery step 58 can use any conventional technique for extracting the oil value in the solids portion 48, including, for example, chemical extraction, expeller extraction, hydraulic press extraction, carbon dioxide assisted extraction and supercritical fluid extraction. Expeller extraction is preferred. Where supercritical fluid extraction is used, a preferred supercritical fluid is carbon dioxide with or without co-solvents such as propane and/or ethanol. Suitable methods of supercritical fluid extraction are set forth, for example, in U.S. Pat. No. 4,495,207 to Christianson et al., which is incorporated by reference herein.

The remaining high protein solids 60 are then combined as mentioned above with the concentrated stream 62 from evaporation step 52 to yield the high protein feed product 54.

What is claimed is:

1. An improved grain milling process including the production of ethanol by fermentation, comprising:
   grinding a whole grain;
   forming a slurry with water of the ground whole grain;
   adding one or more enzymes and one or more organic acids to the slurry with heating to liquefy fermentable components of the ground whole grain and produce a mash;
   recovering and recycling at least a portion of the one or more organic acids used to produce the mash;
   adding an enzyme to the mash to form a fermentation medium for producing ethanol; and
   fermenting the fermentation medium in the presence of yeast and one or more added enzymes.

2. A process as described in claim 1, wherein the one or more organic acids are added in the form of a solution of acetic acid, formic acid or a combination of acetic and formic acids in water.

3. A process as described in claim 2, wherein the aqueous organic acid solution is 50 percent or more by weight of acid.

4. A process as described in claim 3, wherein the aqueous acid solution is from 50 to 70 percent by weight acid in water.

5. A modified dry grind process for milling a whole grain in order to produce ethanol by fermentation, comprising:
   grinding a whole grain;
   forming a slurry of the ground whole grain in from two to three times the weight of the ground whole grain of water;
   adding an aqueous solution of 50 percent by weight and greater of acetic acid or formic acid or both to the slurry, while maintaining the temperature of the slurry at from 70 degrees Celsius to 90 degrees Celsius;
   adding α-amylase enzyme and increasing the slurry's temperature to from 105 to 110 degrees Celsius for from 5 to 15 minutes;
   reducing or allowing the temperature of the resulting mash to cool to between 60 and 75 degrees Celsius;
   adding glucoamylase enzyme to the mash, with maintaining a temperature of between 60 and 75 degrees Celsius for from 1 to 48 hours;
   fermenting the resultant fermentation medium with the addition of one or more of glucoamylase, hemicellulases, proteases, cellulases and feruloyl esterases and yeast to produce ethanol; and
   recovering the ethanol.

6. A process as described in claim 5, further comprising recovering at least a portion of the added acetic acid or formic acid or both before the addition of the glucoamylase enzyme to the mash, and recycling recovered acetic acid or formic acid or both for combining with the slurry of the ground whole grain.

* * * * *